United States Patent [19]

Farren

[11] Patent Number: 4,467,213

[45] Date of Patent: Aug. 21, 1984

[54] SOURCE ASSEMBLY FOR GAS ANALYSIS INSTRUMENTS

[75] Inventor: Carl A. Farren, Placentia, Calif.

[73] Assignee: Beckman Instruments, Inc., Fullerton, Calif.

[21] Appl. No.: 392,841

[22] Filed: Jun. 28, 1982

[51] Int. Cl.³ .............................................. G01J 1/00
[52] U.S. Cl. .............................. 250/504 R; 250/493.1; 350/275
[58] Field of Search .................. 250/503, 504 R, 493, 250/494, 351; 350/1.1, 6.5, 273, 274, 275; 313/113, 114

[56] References Cited

U.S. PATENT DOCUMENTS

| | | |
|---|---|---|
| 2,648,249 | 8/1953 | Canada . |
| 2,754,424 | 7/1956 | Woodhull et al. . |
| 3,023,662 | 3/1962 | Hicks ................................... 350/6.5 |
| 3,107,300 | 10/1963 | Stanley et al. . |
| 3,144,555 | 8/1964 | Aroyan et al. . |
| 3,574,445 | 4/1971 | Harmon ............................. 350/275 |
| 3,729,264 | 4/1973 | Simazaki et al. . |
| 3,915,019 | 10/1975 | Zoltan ................................. 74/5.6 A |
| 3,918,714 | 11/1975 | Ceccaroni . |
| 3,932,041 | 1/1976 | Staab . |
| 3,978,342 | 8/1976 | Hagen et al. ...................... 250/494.1 |

Primary Examiner—Bruce C. Anderson
Attorney, Agent, or Firm—R. J. Steinmeyer; P. R. Harder; E. C. Jason

[57] ABSTRACT

An improved source assembly for use in infrared gas analysis instruments. A rotating reflector having a generally conical shape is provided with a reflective interior surface. An infrared source directs infrared radiation against the reflector from a predetermined number of fixed directions each of which is generally perpendicular to its axis. One or more blocking members, which are aligned generally parallel to the axis of the reflector, pass between the source and the reflective surface as the reflector is rotated. In operation the source assembly generates a plurality of chopped beams of infrared radiation which, because they emanate from a single source and are reflected from the same reflective surface, have a highly uniform intensity. This uniformity of intensity allows the source assembly to illuminate a plurality of sample cells that are distributed circumferentially about the axis of the reflector. The result is an instrument having improved response at a cost that is less than that of a source assembly that includes multiple infrared sources.

23 Claims, 21 Drawing Figures

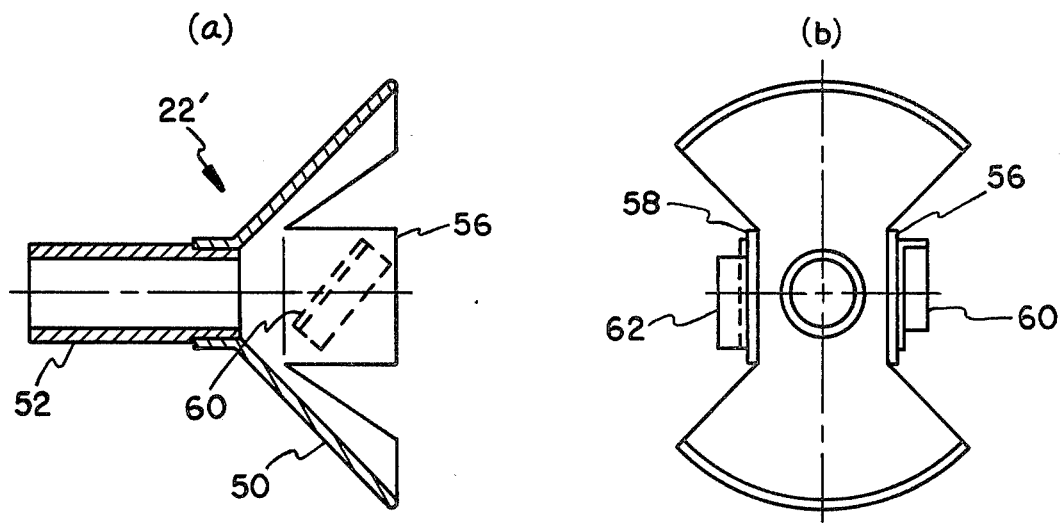
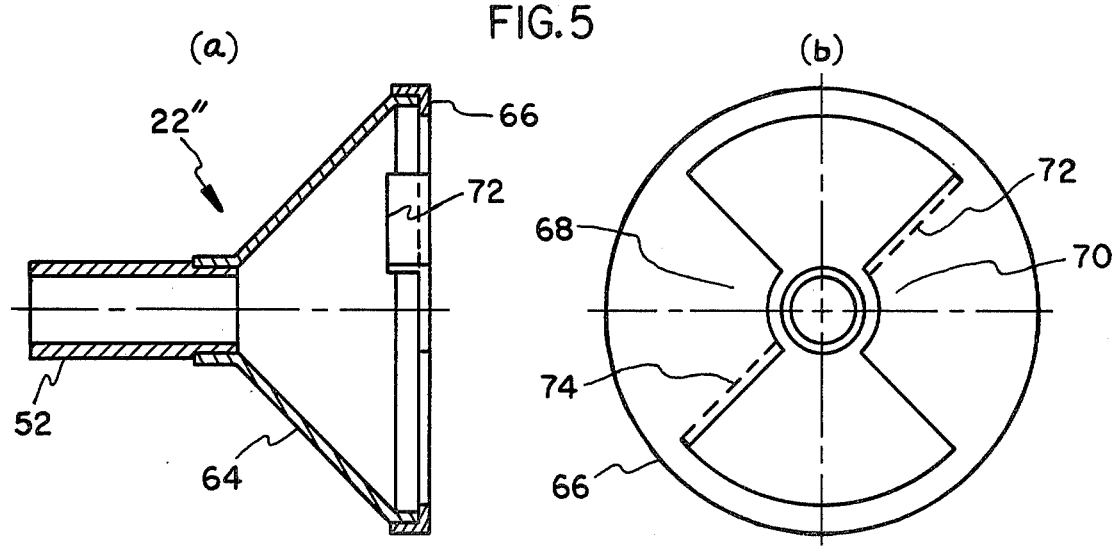
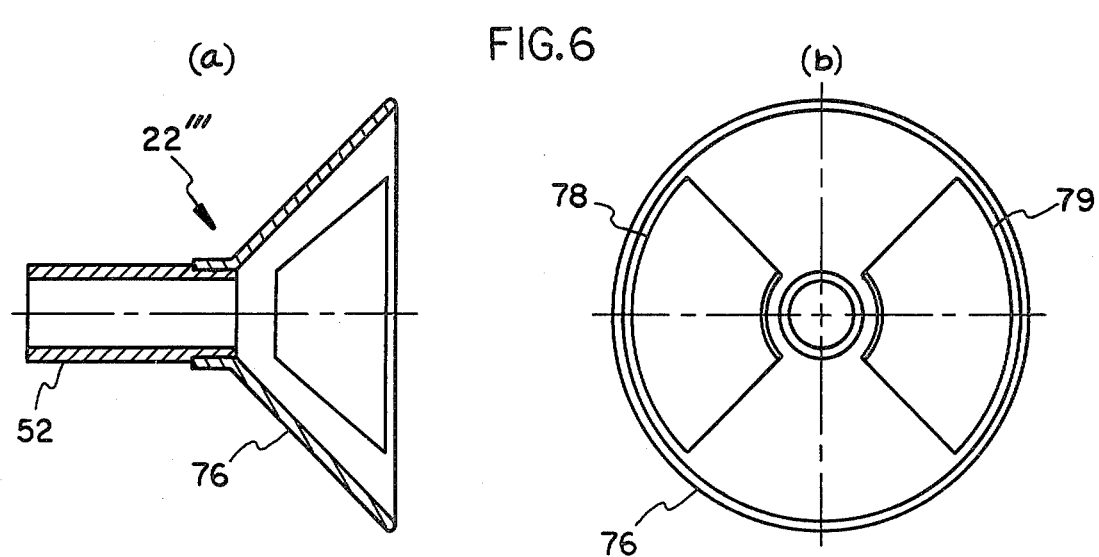

SOURCE ASSEMBLY FOR GAS ANALYSIS INSTRUMENTS

BACKGROUND OF THE INVENTION

Instruments which measure the concentration of a component of a sample gas often operate by measuring the absorption of infrared radiation passing through the sample gas. In particular, such instruments direct a flow of the sample gas through a sample cell having infrared transparent windows and irradiate that cell with infrared radiation. Since the component of interest will absorb infrared radiation at characteristic ones of the wavelengths emitted by the source, a fraction of the incident radiation will be absorbed thereby, the fraction depending upon the concentration of the component of interest. By measuring the quantity of radiation that is transmitted through the sample cell with, for example, a thermistor or Luft-type detector, the quantity of infrared radiation that is absorbed by the gas in the sample cell, and therefore the concentration of the component of interest, may be determined.

In order to provide an infrared intensity reference for such measurements, it is customary to include in the instrument a reference cell which is irradiated by a separate infrared source. Because the reference cell and source are similar to the sample cell and source, except for the fact that the reference cell does not contain any of the component of interest, the level of radiation transmitted through the reference cell provides a convenient reference or standard against which to compare the level of radiation transmitted through the sample cell. This referencing of the output of the sample cell to the output of the reference cell is usually accomplished either by comparing the outputs of two similar detectors which are positioned at the output ends of the two cells, or by providing a differential detector the output of which varies in accordance with the difference between the outputs of the two cells.

In instruments of the above-described type, a chopper disc is usually placed between the sample and reference cells and their respective infrared sources to modulate the intensity of the applied radiation. By rotating this chopper disc at a frequency of, for example, 10 Hz, a 10 Hz signal component is introduced into the output signals of the infrared detectors. By then passing the modulated detector output signals through a 10 Hz band pass filter, much of the high and low frequency noise that is present in those signals is eliminated. One instrument of the above-described type is shown in U.S. Pat. No. 3,729,264, issued on Apr. 24, 1973 in the name of Simazaki et al.

In spite of their advantages, instruments which use the above-described dual-cell, dual-source arrangement have several shortcomings which limit their performance and make them inconvenient to use. One of these shortcomings is that the intensity of the radiation from the two sources may not be the same. As a result, the output of the reference cell detector may cause the output of the sample cell detector to appear to be larger or smaller than is actually the case. Even infrared sources which originally provide infrared radiation of equal intensities may not continue to do so with the passage of time.

Another shortcoming of instruments which use the above-described dual-cell, dual-source arrangement is that they require delicate adjustments of the alignment between the infrared sources and the respective cells. In a typical instrument each infrared source is provided with two horizontal adjustment screws for aligning it with the respective cell and a third adjustment screw for adjusting the distance between the source and the cell. Since adjustments of this type are provided for each source, a total of six adjustments may be necessary.

In order to avoid these shortcomings, as well as the cost of providing dual infrared sources, some instruments have been constructed with a single source the output of which is divided among the sample and reference cells by a plurality of passages which converge in the vicinity of the source. One instrument of the latter type is described in U.S. Pat. No. 2,754,424, issued on July 10, 1956 in the name of Woodhull et al. While instruments of the latter type may not have the same short-comings as instruments of the dual-cell, dual-source type, they have disadvantages of their own which limit their utility. One of these is the overall reduction in the intensity of the infrared radiation for all cells that results from the multiple reflections within the various passages. A related disadvantage is the difficulty of providing a plurality of beams of equal intensities after the beams have been transmitted through passages which have differing lengths and differing reflective properties. Such a reduction in infrared intensity has the effect of worsening the signal-to-noise ratio of the instrument and therefore limiting the range at which accurate measurements may be made.

Another disadvantage of utilizing the above passages is the fact that the light that emerges from these passages is poorly collimated. Unlike the dual-source instruments in which parabolic reflectors can be provided for each source to collimate the beams emitted thereby, the radiation emitted by the single source through beam dividing passages is emitted at random angles. As a result, a sizable fraction of the source radiation is reflected from the surfaces of the cell windows, thereby further reducing the intensity of the radiation passing through the cells and further worsening the signal-to-noise ratio of the instrument.

SUMMARY OF THE INVENTION

In accordance with the present invention, there is provided an improved source assembly which produces a plurality of high intensity, highly uniform beams from a single infrared source. In addition, the source assembly of the invention provides infrared beams having a higher degree of collimation than those produced by previously available single-source source assemblies.

Generally speaking, the source assembly of the invention includes a cone-shaped rotating reflector having a reflective interior surface. This reflective surface is illuminated by an infrared source through a channeling member which directs the source radiation against the reflector from a predetermined number of fixed directions. The transmission of radiation from the source to the reflector is interrupted by one or more blocking members which project from the surface of the reflector in a direction that is generally parallel to the axis thereof. When the reflector is rotated, the source, the channeling and blocking members, and the reflective surface cooperate to produce a plurality of chopped infrared beams which are distributed circumferentially about the axis of the reflector. At each of these circumferential positions, the chopped beam is characterized by high intensity and a high degree of uniformity between beams. Thus, the source assembly of the invention provides beams of comparable or better quality than those available from multiple-source instruments and does so without the disadvantages that are associated with previously available single-source instruments.

In the preferred embodiment the channeling member is provided with a plurality of collimating grooves which have the effect of decreasing the tendency of each infrared beam to spread as it propagates down the cell to which it is applied. This is a highly desirable result because in many cases it eliminates the need for providing cells having highly reflective internal walls. The elimination of such reflective walls, in turn, not only makes possible the use of low-cost plastic materials for the cells, but also reduces the extent to which the outputs of the infrared detectors are dependent upon the accumulation of dirt on the cell walls.

In another embodiment of the invention, the channeling member is provided with an alternative collimating arrangement which includes one or more separate light pipe assemblies. These light pipe assemblies may, for example, include coils of corrogated metal or optical fiber bundles which provide a multiplicity of parallel optical paths each of which is aligned with the desired optical path between the source and the reflector. The effect of these parallel optical paths is generally similar to those of the previously mentioned collimating grooves. Because the number of paths is greater, however, the collimating effect (and cost) is also greater.

In addition to providing the above-described benefits, the source assembly of the invention eliminates the need for adjustments of the alignment between the source and the sample and reference cells. This is because the positions of the various parts of the source assembly and the positions of the cells are all uniquely fixed by the position of the axis of rotation of the reflector. The infrared source is, for example, colinear with the axis of the reflector while the sample and reference cells are each parallel to and equidistant from that axis. Since these relationships to the axis are established at the time of manufacture, an instrument constructed in accordance with the present invention does not require any of the alignment adjustments that characterized previously known source assemblies.

In accordance with another feature of the present invention, the above-mentioned blocking member may be made to serve as a light concentrating element as well as a light interrupting element. In particular, in those embodiments in which an odd number of blocking members are present, the same element which blocks radiation when it is positioned between the source and the cells serves as a radiation reflector and concentrator when it is positioned so that the source lies between it and the cell. This assures that more infrared radiation is provided to the cell at a given source power level or, alternatively, that the same level of radiation may be provided to the cell with a reduced source power level.

In accordance with still another feature of the present invention, the reflector includes a cylindrical base member which may be formed as an integral part of the rotor of the motor which drives the reflector. This integral reflector-rotor construction, in turn, eliminates the need for a shaft to join the reflector to its drive motor and thereby reduces the overall length of the source assembly. Particularly when used with an infrared source that projects into the open end of the reflector, the result is a source assembly having an overall length that is hardly twice the length of the drive motor alone. As a result of this compactness, the cells of the instrument may be made longer for a given instrument housing size than would be the case with a bulkier source assembly. This is an advantage because the signal-to-noise ratio of infrared gas measuring instruments is proportional to the length of its cells.

DESCRIPTION OF THE DRAWINGS

Other objects and advantages of the invention will be apparent from the following description and drawings in which:

FIG. 9a is a simplified cross-sectional view of a two-source embodiment of the invention; FIG. 9b is a front view of the mounting member of FIG. 9a.

DESCRIPTION OF THE PREFERRED EMBODIMENTS

Figure 1:
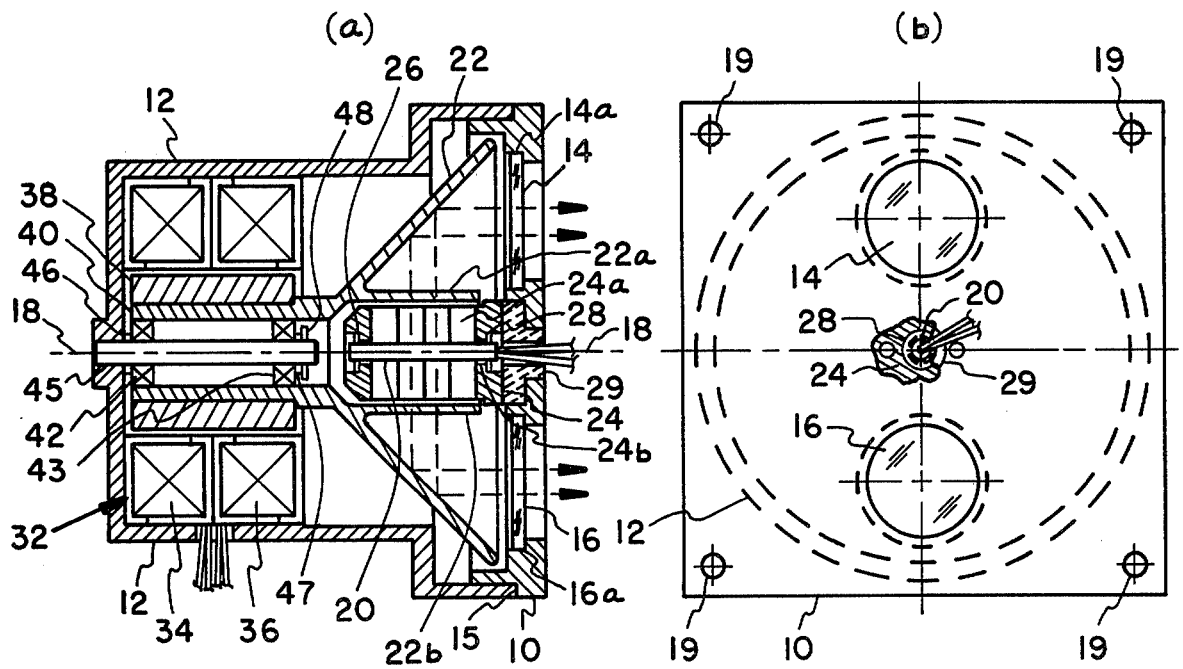
FIGS. 1a and 1b are side cross-sectional and front views of the preferred embodiment of the source assembly of the invention.

Referring to FIGS. 1a and 1b, there is shown a side cross-sectional and front view of the preferred embodiment of the source assembly of the invention. As is best seen in FIG. 1a, the source assembly includes a housing having a front section 10 and a rear section 12. Front housing section 10 includes a plurality of infrared transparent windows 14 and 16 through which infrared radiation may be provided to a reference cell and a sample cell, respectively, of a cell assembly of a known type (not shown). Windows 14 and 16 are preferably located at equal distances from the central axis 18 of the source assembly, with the cells of the cell assembly being located at similar equal distances from its own central axis. The desired alignment between the sources and the cell assembly is then established when the axis of the source assembly is aligned with that of the cell assembly by aligning the mounting holes 19 by which the two assemblies are joined. Thus, no alignment adjustments are necessary with the source assembly of the invention.

Infrared transparent windows 14 and 16 are preferably sealably mounted in respective openings 14a and 16a of housing section 10. Similarly, housing sections 10 and 12 are preferably sealably joined at a junction 15. This assures that the housing of the source assembly of FIG. 1 forms a substantially air-tight enclosure that protects the interior of the source assembly against the entry of dirt and polluting gases that might affect the intensity of the radiation provided thereby.

To the end that windows 14 and 16 each provide a chopped beam of infrared radiation, the source assembly of FIG. 1 includes a generally cylindrical infrared source 20 having a center line that is substantially colinear with axis 18, and a generally conical shaped rotating reflector 22 having an axis of rotation that is also substantially colinear with axis 18. Because the inner surface of the conical portion of reflector 22 forms an angle of 45° with axis 18, it will be seen that, when no obstruction is present between the source 20 and reflector 22, the radiation which source 20 emits in a direction perpendicular to axis 18 will be reflected from the inner surface of reflector 22 to emerge in a direction that is parallel to axis 18. The path of the part of this radiation that emerges from windows 14 and 16 is indicated by the dotted lines shown in FIG. 1a.

Since the intensity of the output radiation of the source assembly is preferably as high as possible, the inner surface of reflector 22 is preferably polished or provided with a reflective coating to afford a high reflectivity at infrared wavelengths. The intensity of this radiation is further increased by providing a member 24 which mounts source 20 and channels the output radiation thereof in those predetermined fixed directions which will result in the reflection of infrared radiation through windows 14 and 16. More particularly, as is most clearly seen in the isometric and top views of FIGS. 3a and b, member 24 is provided with an aperture 24a which may be formed by a plurality of overlapping holes. When member 24 is bolted to housing section 10 via mounting holes 30 and 31, aperture 24a is oriented in a direction that is perpendicular to axis 18. Because of this orientation, and because member 24 lacks openings that would allow radiation to emerge in other directions, radiation from source 20 will be channeled towards reflector 22 in those directions which will result in its being reflected through windows 14 and 16. This channeling effect is preferably further enhanced by polishing or providing a reflective coating on the sides of the holes that form aperture 24a to increase their reflectivity.

In order to minimize the conduction of heat into mounting member 24, source 20 is mounted therein by means of stand-off clips 26 and 28. These clips center and hold source 20 within a hole 24b through member 24 without allowing it to directly touch the same. The true shape of the these clips is most clearly seen in FIG. 3a. The conduction of heat from source 20 into housing section 10 through member 24 is preferably kept to a minimum by providing a separator 29, composed of a thermally nonconductive ceramic material, between member 24 and housing section 10.

Figure 2:
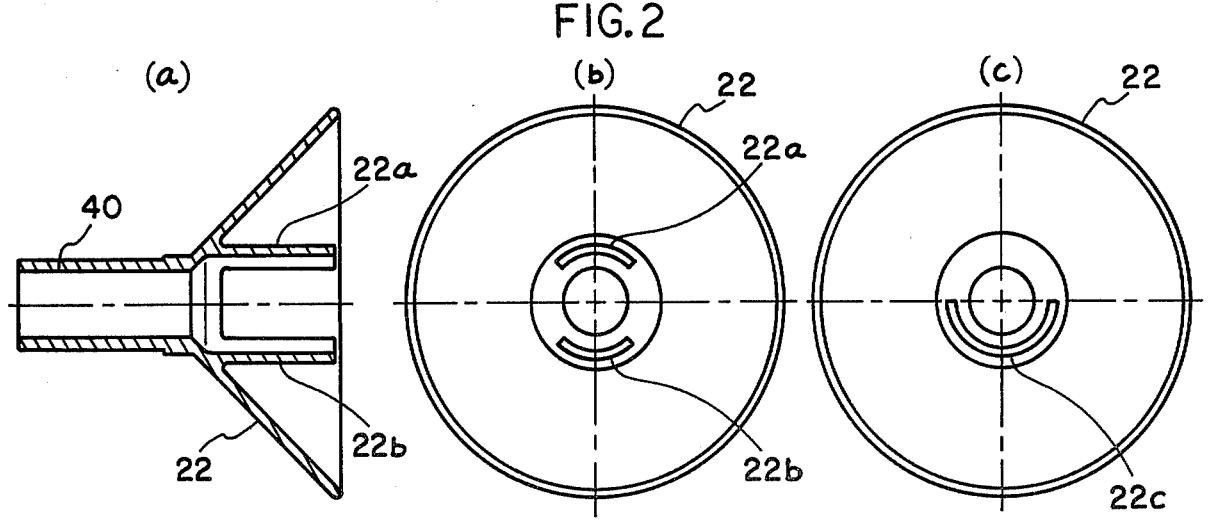
FIGS. 2a and 2b are cross-sectional and front views of the reflector of FIG. 1.
FIG. 2c is a front view of an alternative embodiment of the reflector of FIG. 1, FIGS. 3a and 3b are isometric and top views of the channeling-collimating member of FIG. 1, FIGS. 4, 5, and 6 are cross-sectional and front views of still other embodiments of the reflector of FIG. 1.

To the end that the rotation of reflector 22 may chop (i.e., interrupt) the beams of infrared radiation which are reflected through windows 14 and 16, reflector 22 is provided with blocking members 22a and 22b, which are most clearly seen in FIGS. 2a and b. When, as shown in FIG. 1a, reflector 22 is in a rotational position in which blocking members 22a and 22b interpose themselves between aperture 24a and the reflective surface of reflector 22, the reflection of infrared radiation through windows 14 and 16 is blocked. When, on the other hand, reflector 22 is in a rotational position in which members 22a and 22b do not interpose themselves between aperture 24a and the reflective surface of reflector 22, intense beams of radiation are reflected through windows 14 and 16. It will therefore be seen that as reflector 22 is rotated, blocking members 22a and 22b alternately assume their blocking and unblocking positions to chop the radiation emerging through windows 14 and 16. It will be noted that because there are two blocking members 22a and 22b and two open spaces between them, two bursts of infrared radiation will be transmitted through each of windows 14 and 16 for each full revolution of reflector 22. Thus, the motor 32 which drives reflector 22 should operate at a rotational speed that corresponds to one-half of the desired chopping frequency.

Conical reflector 22 may also, however, be provided with a single blocking member 22c, as shown in FIG. 2c. In the latter embodiment, blocking member 22c is a generally half-cylindrical member which blocks transmission through one of windows 14 and 16 during half of each revolution of reflector 22, and blocks the transmission of radiation through the remaining window during the remainder of each revolution. Naturally, with this blocking arrangement, the reflector 22 of FIG. 2c must be driven at a rotational speed that corresponds to the full desired chopping frequency.

The advantage of using the reflector of FIG. 2c is that the inner (concave) surface of blocking member 22c is able to reflect radiation from source 20 back along the longitudinal axis of aperture 24a to increase the intensity of the radiation which source 20 transmits toward reflector 22. As a result, blocking member 22c serves not only to interrupt the reflection of radiation by reflector 22 for one-half revolution thereof, but also to increase the intensity of the radiation that is reflected thereby during the remaining half revolution thereof. In order to derive the maximum possible benefit from the dual blocking-reflecting action of member 22c, it is preferred that the inner surface thereof be polished or coated to increase its infrared reflectivity.

In general, the ability of a blocking arrangement to provide the above-described dual action is not limited to embodiments having a single blocking member. On the contrary, the dual ability to sequentially block and intensify radiation will be exhibited by any reflector having an odd number of blocking members. This is because, when one blocking member is reflecting radiation, it is necessary for the diametrically opposite surface of the reflector 22 be unblocked to provide a clear path for the reflection of radiation to the source assembly outlet windows. It will therefore be understood that the number and spacing of the blocking members may vary from application to application without departing from the teachings of the present invention.

Reflector 22 may be rotated by any suitable driving means having the desired rotational speed stability. In the preferred embodiment this driving means comprises an a-c motor 32 which, except for the manner of its attachment to reflector 22, is of a conventional commercially available type. In particular, motor 32 includes two side-by-side stator coils 34 and 36, and a magnetic rotor 38 having a plurality of permanently magnetized regions located around the periphery thereof. Motor 32 may, for example, comprise a 48-pole stepper motor which, when supplied with the recommended drive voltages, rotates rotor 38 at 10 revolutions per second.

In the preferred embodiment, the overall length of the source assembly is reduced by replacing the interior of rotor 38 with a cylindrical base member 40 which is integral with and projects from the vertex of the conical portion of reflector 22. Cylindrical base member 40 may, for example, be press fit within the interior of rotor 38. Then, after the housing of stator coils 34 and 36 is mounted within housing section 12, the previously mentioned reflector-rotor subassembly may be rotatably positioned within the stator assembly by any suitable means. One such means includes bearings 42 and 43, which are press-fit within a hole 44 in base member 40 (see FIG. 2a), and a bearing shaft 45 which is mounted in housing section 12. The reflector-rotor subassembly is conveniently retained on shaft 45 by wave washers 46 and 47, and a retaining ring 48. It will, however, be understood that any other suitable bearing structure, such as needle bearings, which will support the rotation of reflector 22 may also be used.

Because motor 32 rotates at a speed that depends only upon the frequency of the a-c voltage and the number of its poles, reflector 22 will provide chopped infrared radiation having a highly stable frequency. In addition, because the infrared radiation from the source assembly originates in a single source 20 and is reflected from a single reflecting surface, the intensity of the radiation transmitted through window 14 is closely matched to that transmitted through window 16. Together these features are highly desirable since they assure both that the radiation applied to the sample cell is accurately referenced to the radiation applied to the reference cell, and that there is no frequency drift or jitter to disturb the operation of the above-mentioned band-pass filter. Thus, the source assembly of the invention provides an improvement in performance in spite of the cost savings resulting from the elimination of one infrared source and the energy required to operate the same.

Because base member 40 of reflector 22 occupies the interior of rotor 38, and because source 20 projects into the interior of reflector 22, the source assembly of FIG. 1 is extremely compact. This compactness is advantageous because it allows the cells of the cell assembly may be made longer than would be the case if the source assembly were less compact. The longer cell length, in turn, improves the signal-to-noise ratio of the signals produced by the detectors that receive radiation through those cells. Thus, the source assembly of the invention makes possible an improvement in the signal-to-noise ratio of the instrument with which it is used.

Referring to FIGS. 4, 5, and 6, there are shown three of many possible alternative embodiments for reflector 22. Referring to FIG. 4a and b, for example, there is shown a reflector 22' having a conical section 50, and a separate cylindrical base section 52, the latter two sections being attached by for example welding. The radiation interrupting function of the reflector of FIG. 4 is served by blocking members 56 and 58, which correspond to blocking members 22a and 22b of FIG. 2.

It might be observed that because conical section 50 of the reflector of FIG. 4 is discontinuous, i.e., does not include a complete surface of revolution, blocking members 56 and 58 might be omitted, since the missing portions of conical section 50 will themselves interrupt the reflection of radiation from reflector 22. While there is some truth in the latter statement, it is also true that, in the absence of blocking members 56 and 58, there will be an increase in the level of background radiation within the source assembly. The increased background radiation will, in turn, result in an increase in the level of background radiation in the cell assembly. Thus, while blocking members 56 and 58 are not absolutely essential in the embodiment of FIG. 4, their presence is nevertheless desirable.

One practical advantage which the reflector of FIG. 4 has over that of FIG. 1 is that the reflector of FIG. 4 lends itself to fabrication by stamping. With such a stamping process, blocking members 56 and 58 can be formed at the same time and from the same material as the reflecting surface of reflector 50. A second advantage of the reflector of FIG. 4 is that it is easily provided with fan blades 60 and 62 which may be spot welded to blocking members 56 and 58 after the latter have been formed. These fan blades are beneficial in that they impart a forced circulation to the air in the interior of the source assembly. This forced circulation in turn aids in the out-flow of heat from the source assembly and therefore allows it to run cooler. It will be understood that these fan blades may also be provided for the reflector 22 of FIG. 2, as integral molded or cast features.

Referring to FIG. 5, there is shown another embodiment 22" of a reflector that may be used in the source assembly of the invention. Reflector 22" of FIG. 5 is similar to that of FIG. 4 in that it includes a cylindrical base member 52 which is attached to a stamped conical section 64. The embodiment of FIG. 5 differs from that of FIG. 4, however, in that stamped conical section 64 thereof constitutes a complete surface of revolution. Reflector 22" of FIG. 5 also differs from that of FIG. 4 in that it includes a circular cover plate 66 which includes generally wedge-shaped projections 68 and 70 which serve the radiation-interrupting function of blocking members 56 and 58 of the embodiment of FIG. 4. Cover plate 66 may also be provided with fan blades 72 and 74 which serve the same function as fan blades 60 and 62 of the embodiment of FIG. 4. Thus, in spite of some structural differences, the reflector 22" of FIG. 5 is the functional equivalent of reflector 22' of FIG. 4.

Referring to FIG. 6, there is shown still another alternative embodiment 22''' of a reflector which may be used in the source assembly of the invention. Like the reflectors of FIGS. 4 and 5, the reflector of FIG. 6 includes a cylindrical base section 52 which is attached to a stamped conical section 76. The reflector of FIG. 6, however, interrupts the transmission of radiation from source 20 to windows 14 and 16 by means of the wedge-shaped apertures 78 and 79, rather than by means of the wedge-shaped projections of FIG. 5. In spite of its usability, the reflector of FIG. 6 is not preferred. This is because of the higher level of infrared background radiation which will be present within the source assembly when reflector 22''' is used.

Figure 3:
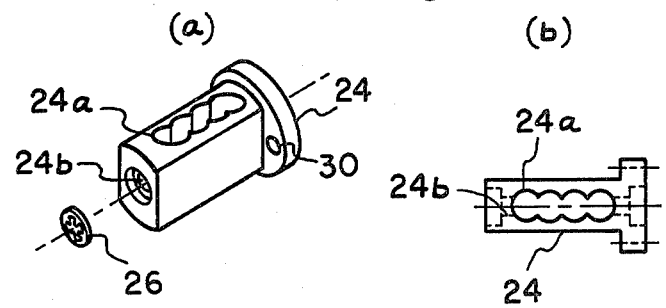
Figure 7:
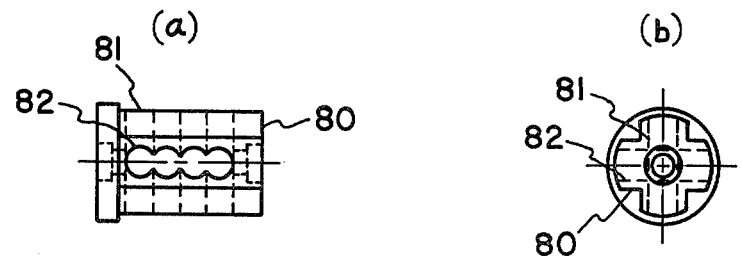
FIG. 7 is an alternative embodiment of the channeling-collimating member of FIG. 3, FIG. 8a and 8b are front and side views of a channeling member having an alternative collimating arrangement.

Referring to FIG. 7, there is shown an alternate embodiment for mounting member 24 of FIG. 3. The mounting member 80 of FIG. 7 is similar to that of FIG. 3, except that it includes an aperture arrangement that channels infrared radiation from source 20 in four rather than two directions. In particular, member 80 includes a first aperture 81 which is similar to aperture 24a of the embodiment of FIG. 3, and a second aperture 82 which is similar to aperture 81, but which is oriented in a direction that is generally perpendicular thereto. Because mounting member 80 channels radiation against its associated reflector from four directions, the source assembly may have four rather than two outlet windows. This, in turn, makes it possible to use the source assembly of the invention with a cell assembly that includes three separate sample cells and a reference cell, i.e., an instrument which simultaneously measures the concentration of the three different components of interest in the sample gas.

In general, provided only that an appropriate number of outlet windows are distributed around the circumference of the circle traced out by the reflector (all at equal distances from axis 18), the number of cells that may be excited by the source assembly may be three or five or even more. Naturally, in such cases, the mounting element must channel radiation against the reflector from a corresponding number of fixed directions and must, therefore, be provided with apertures that are aligned with such directions. In addition, in such cases, it may be necessary to adopt a different number and spacing for the blocking members in order to assure the desired chopping frequency with the available motor speed. Because of the straightforward nature of such modifications, these further embodiments will not be described in detail or shown herein.

As explained previously in connection with FIG. 3, mounting member 24 serves to channel or concentrate radiation from source 20 in those directions which result in transmission through windows 14 and 16. In addition to concentrating this radiation, however, mounting member 24 also serves to collimate it, i.e., to reduce its tendency to spread in a direction perpendicular to the direction of propagation. This collimation results in part from the presence of the parallel curved surfaces (holes) which form the sides aperture 24a, and in part from the curvature of reflector 22. Note in this connection that the centers of curvature of the individual holes of aperture 24a are perpendicular to axis 18, while the center of curvature of reflector 22 is colinear with axis 18. This perpendicularity of the two centers of curvature itself cause the radiation that is reflected from both surfaces to show an increased degree of collimation. Some part of the improvement in the collimation of the radiation is also associated with the fact that the holes making up aperture 24a act to some extent as light pipes. This, in turn, causes these holes to have a straightening effect analogous to that of a flow straightener in a gas flow system. Some improvement in the degree of collimation is even afforded to radiation that is transmitted through aperture 24a without being reflected from the sides thereof. This is because the natural tendency of such radiation to diverge is offset in part by the concavity of reflector 22. Together, in spite of the absence of a bulky and costly optical system, the collimating properties of mounting member 24 and/or reflector 22 provide a degree of collimation which is greatly improved over that provided by sources which shine directly into respective cells.

The advantage of illuminating the cell assembly with a collimated source is that it reduces the extent to which the cell assembly relies upon reflections from the interior surfaces of the cell walls to provide a high level of infrared radiation to the detectors. Since a significant portion of the radiation from the source assembly of the invention is collimated, the need for cells having highly reflective interior surfaces is substantially reduced. As a result, the cells that are used with the source assembly of the invention may in many cases be constructed without plated gold reflective interiors. This, in turn, reduces the cost of the instrument without a corresponding worsening in the performance thereof.

If plated reflective surfaces are already present in the cells, it is possible to practice the invention with a mounting member that does not have holes which impart above-described light pipe action. In such embodiments, mounting aperture 24a may be constructed with a simple polished or unpolished aperture slot to reduce the cost thereof. In such cases, the collimating effect will be significantly reduced, but mounting member 24 will still have the beneficial effect of channeling radiation from source 20 in directions in which it will be reflected through windows 14 and 16.

Figure 8:
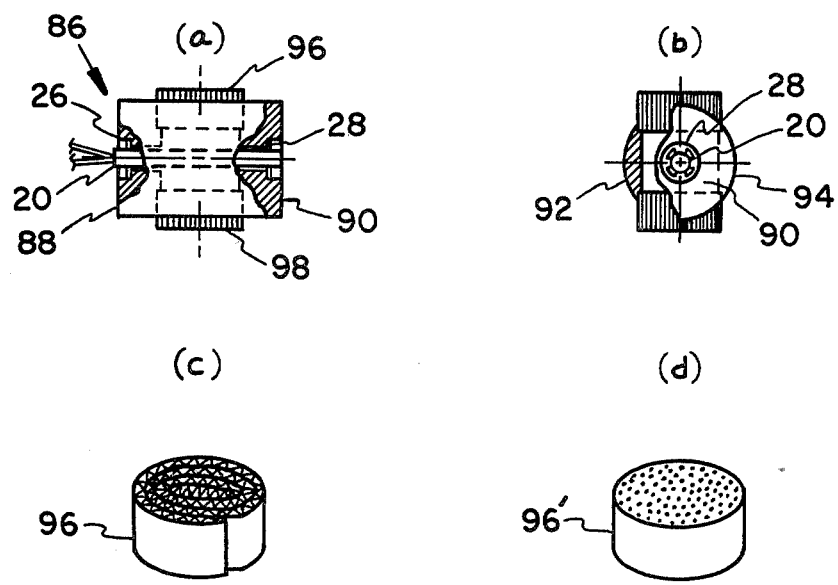
FIGS. 8c and 8d are views of two different collimating elements that may be used in the member of FIGS. 8a and b.

On the other hand, where the collimating effect of mounting member 24 is critical to the performance of the instrument, the collimating effect of the source assembly may be enhanced by replacing mounting member 24 of FIG. 3 with a higher-performance mounting member of the type shown in FIGS. 8a and b. Referring to FIG. 8a, there is shown a mounting member 86 which is in a number of respects similar to mounting member 24 of FIG. 3. Mounting member 86, for example, mounts source 20 between a base plate 88 and an end plate 90 by means of stand-off clips 26 and 28. In addition, mounting member 86 produces the above-described channeling effect by channeling radiation from source 20 between side plates 92 and 94, which are best seen in FIG. 8b. The embodiment of FIG. 8 differs from that of FIG. 3, however, in that it includes separate collimating elements 96 and 98 which rest on respective shoulders in side plates 92 and 94. These collimating elements preferably comprise high-performance light pipe arrangements, two examples of which are shown in FIGS. 8c and d.

In the embodiment of FIG. 8c, collimating element 96 comprises a strip of a shiny corrogated metal which has been wound into a coil. In this embodiment the corrugations define a multitude of parallel light pipes which increase the collimation of the radiation passing therethrough in generally the same manner as the curved surfaces of aperture 24. As a result, the rays that enter one end of collimating element 96 at a wide range of angles emerge from the opposite end thereof in a more nearly collimated beam. Those rays which do emerge from collimating element 96 and form large angles with the axis thereof are quickly scattered and therefore do not remain in the beam that is reflected from reflector 22 through windows 14 and 16. As a result, mounting member 86 of FIG. 7 provides a degree of collimation which is higher than that available from mounting member 24 of FIG. 3.

Another collimating element that may be used in the mounting member 86 of FIG. 8 is the collimating element 96' of FIG. 8d. This collimating element is composed of a plurality of bound optical fibers each of which is aligned in a direction parallel to the axis of element 96'. Collimating elements of this type are preferably made by aligning a plurality of optical fibers in a cylindrical form, binding them together with a suitable resin, and then cutting and polishing the desired lengths of material therefrom. Because optical fibers having very small diameters are readily available, the collimating element 96' of FIG. 8d can be made with a much greater number of light pipes than even the collimating element 96 of FIG. 8c. As a result, collimating element 96' can provide an even stronger collimating effect than collimating element 96, although at a somewhat greater cost.

While the above-described collimating elements are preferably located in the immediate vicinity of source 20, this is not the only position in which collimating elements will produce a beneficial effect. It is also possible to place the collimating elements beyond the blocking members of the reflector, such as, for example, in series with outlet windows 14 and 16.

Figure 9:
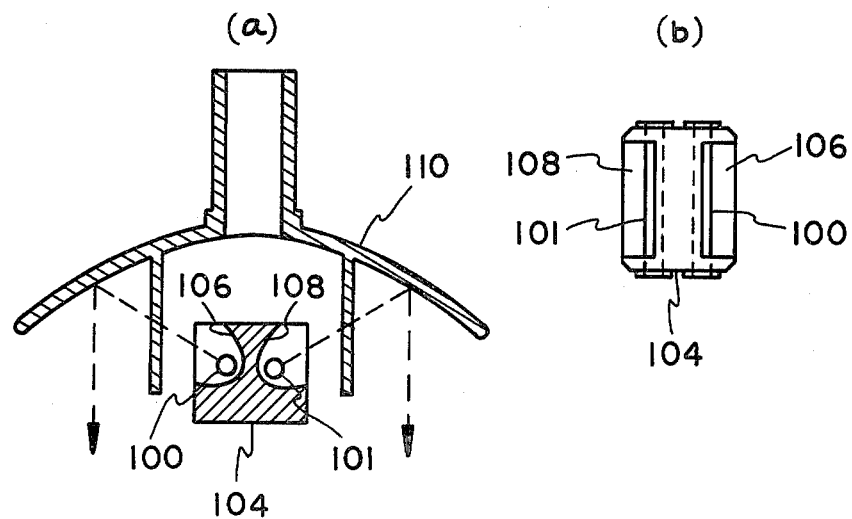

Although the preferred embodiments of the present invention contemplate the use of a single infrared source, there is no reason in principle that two infrared sources could not be used. One embodiment of such a two-source embodiment is shown in FIGS. 9a and b. As shown in FIG. 9a, the latter embodiment includes two infrared sources 100 and 101 which are both mounted in a mounting member 104, in respective channeling recesses 106 and 108. The latter recesses, which preferably have a parabolic cross section, not only channel but also concentrate and collimate the beams directed at reflector 110. In order to increase the collimation further, the reflective surface of reflector 110 may be configured as a parabolic rather than a conical surface of revolution. The principal advantage of the embodiment of FIG. 9 is that it provides infrared output beams of higher intensity than those of the single source embodiments. The principal disadvantage of the embodiment of FIG. 9 is that it provides infrared beams that are more poorly matched than those of the single source embodiments.

In view of the foregoing, it will be seen that a source assembly constructed in accordance with the present invention has a number of advantages over previously available source assemblies. Firstly, the source assembly of the invention provides a plurality of infrared beams having closely matched intensities from a single infrared source. Secondly, the source assembly of the invention includes means for channeling and collimating the infrared radiation in the various beams, thereby reducing or eliminating the need for cells having highly reflective interior walls. Thirdly, the source assembly of the invention includes a plurality of blocking members which provide the desired chopping action and at the same time reduce the level of background radiation within the source assembly. Finally, in embodiments having an odd number of these blocking members, the intensity of the output radiation of the source assembly is further increased by employing reflections from the inner surfaces of the blocking members to direct additional infrared radiation through the outlet windows.

What is claimed is:

1. An improved source assembly for generating chopped infrared radiation for application to the cells of a gas analysis instrument comprising:
   (a) a generally conical reflector having a reflective inner surface;
   (b) drive means for rotating the reflector;
   (c) an infrared source positioned within the reflector for illuminating the reflective surface;
   (d) channeling means positioned between the source and the reflector for insulating the source and for channeling infrared radiation toward the reflective surface in at least one direction that is generally perpendicular to the axis of rotation of the reflector; and
   (e) means for interrupting the reflection of infrared radiation from the reflective surface when the reflector is in predetermined angular positions.

2. The source assembly of claim 1 in which the reflector has a generally cylindrical base and in which the base is connected to the drive means.

3. The source assembly of claim 2 in which the drive means comprises an a-c motor having a cylindrical rotor, and in which the base occupies the interior of the rotor.

4. The source assembly of claim 1 in which the reflector includes a continuous conical surface, and in which the interrupting means comprises at least one blocking member that projects from the conical surface in a direction generally parallel to said axis.

5. The source assembly of claim 4 in which there are an odd number of blocking members, and in which those surfaces of the blocking members that face the source are polished to reflect additional radiation toward the reflector.

6. The source assembly of claim 1 in which the reflector includes a discontinuous conical surface and in which the interrupting means comprises at least one blocking member that projects from the conical surface in a direction generally parallel to said axis.

7. The source assembly of claim 1 in which the interrupting means comprises at least one opening in the conical surface.

8. The source assembly of claim 1 in which the reflector includes a continuous conical surface and in which the interrupting means comprises a generally circular cover that is attached to the conical surface and includes at least one opening through which infrared radiation may be reflected.

9. The source assembly of claim 1 including a plurality of fan blades attached to the reflector for circulating the air within the source assembly.

10. The source assembly of claim 1 in which the channeling means includes at least one aperture, each aperture including a plurality of collimating grooves for increasing the collimation of the radiation output by the source assembly.

11. The source assembly of claim 1 in which the channeling means includes at least one aperture, each aperture including a plurality of light pipes which are aligned in a direction that is generally perpendicular to the axis of the reflector.

12. An improved source assembly for applying chopped infrared radiation to a gas analysis instrument comprising:
   (a) a generally conical reflector having a reflective inner surface;
   (b) drive means for rotating the reflector;
   (c) an infrared source for illuminating the reflective surface positioned within the reflector,
   (d) a collimating member positioned between the infrared source and the reflective surface,
   (e) said reflective surface including at least one angular region from which substantially no infrared radiation is reflected,
   (f) means for blocking the reflected radiation from said reflector when said reflector is in a predetermined angular positions.

13. The source assembly of claim 12 in which the axis of rotation of the reflector is substantially parallel to the direction in which infrared radiation emerges from the source assembly.

14. The source assembly of claim 12 in which the reflector has a generally cylindrical base that extends from the vertex of the conical surface and in which the base is connected to the drive means.

15. The source means of claim 14 in which the drive means comprises a motor with a cylindrical rotor and in which the cylindrical base occupies the central portion of the rotor.

16. The source assembly of claim 12 in which the reflector includes at least one blocking member that projects from the reflective surface in a direction parallel to said axis, and in which said at least one angular region comprises those portions of the conical surface that fall in the infrared shadows of the blocking members.

17. The source assembly of claim 12 in which the said at least one angular region comprises an opening in the conical surface.

18. The source assembly of claim 12 in which the reflector includes a generally circular cover having at least one opening, and in which infrared radiation emerges from the source assembly through such openings.

19. The source assembly of claim 12 including a plurality of fan blades attached to the reflector for circulating the air within the source assembly.

20. The source assembly of claim 12 in which the collimating member includes a plurality of apertures through which the infrared source may emit radiation only in respective fixed directions.

21. The source assembly of claim 20 in which each aperture is provided with a plurality of curved surfaces which are aligned in a direction that is generally perpendicular to said axis.

22. The source assembly of claim 12 in which the collimating member includes a plurality of light pipes and means for mounting the light pipes between the infrared source and the reflective surface.

23. The source assembly of claim 16 in which there are an odd number of blocking members and in which those surfaces of the blocking members which face the infrared source are polished to reflect additional radiation in the direction of the reflector.

* * * * *